(12) United States Patent
Kaditz et al.

(10) Patent No.: US 11,872,025 B2
(45) Date of Patent: Jan. 16, 2024

(54) SYSTEM AND METHOD FOR MAGNETIC RESONANCE ELASTOGRAPHY (71) Applicant: Q Bio, Inc, San Carlos, CA (US)

(72) Inventors: Jeffrey H. Kaditz, Wilson, WY (US); Andrew G. Stevens, New York, NY (US)

(73) Assignee: Q Bio, Inc., San Carlos, CA (US)

( * ) Notice: Subject to any disclaimer, the term of this patent is extended or adjusted under 35 U.S.C. 154(b) by 560 days.

(21) Appl. No.: 16/085,877

(22) PCT Filed: Mar. 17, 2017

(86) PCT No.: PCT/US2017/022911
§ 371 (c)(1),
(2) Date: Sep. 17, 2018

(87) PCT Pub. No.: WO2017/161239
PCT Pub. Date: Sep. 21, 2017

(65) Prior Publication Data
US 2019/0104963 A1    Apr. 11, 2019

Related U.S. Application Data

(60) Provisional application No. 62/310,667, filed on Mar. 18, 2016.

(51) Int. Cl.
*A61B 5/055* (2006.01)
*G01R 33/563* (2006.01)
(Continued)

(52) U.S. Cl.
CPC ............ *A61B 5/055* (2013.01); *G01R 33/341* (2013.01); *G01R 33/56358* (2013.01); *G06T 7/0012* (2013.01)

(58) Field of Classification Search
CPC ....... A61B 5/055; A61B 8/485; A61B 5/0245; A61B 5/7285; A61B 8/587; A61B 8/58;
(Continued)

(56) References Cited

U.S. PATENT DOCUMENTS 4,729,892 A    3/1988  Beall
5,865,177 A *  2/1999  Segawa ................ G01R 33/341
                                              324/318
(Continued)

FOREIGN PATENT DOCUMENTS

EP         3093677        11/2016

OTHER PUBLICATIONS

Hattori, K., Ikemoto, Y., Takao, W., Ohno, S., Harimoto, T., Kanazawa, S., ... & Kato, H. (2013). Development of MRI phantom equivalent to human tissues for 3.0-T MRI. Medical physics, 40(3), 032303 (Year: 2013).*

(Continued)

*Primary Examiner* — Christopher Koharski
*Assistant Examiner* — Renee C Langhals
(74) *Attorney, Agent, or Firm* — Aurora Consulting LLC; Steven E. Stupp; Ashley Sloat (57) ABSTRACT

An apparatus for use in a magnetic resonance (MR) system for capturing an MR Elastography measurement of a biological lifeform may include a platform; a gel pad on a surface of the platform; and a sensor array. In some embodiments, the sensor array includes at least one ultrasound transducer, and at least one radiofrequency (RF) transmitter and receiver coil. The sensor array is at least partially embedded within the gel pad, and the gel pad is configured to provide mechanical impedance matching between the at least one ultrasound transducer and the biological lifeform. In some embodiments, a system includes the apparatus and an MR system, the MR system including an ultrasonic wave (Continued)

generator, an interface circuit, and a computing device. In some such embodiments, the ultrasonic wave generator is configured to generate one or more shear waves in the biological lifeform.

11 Claims, 7 Drawing Sheets

(51) Int. Cl.
  *G01R 33/341* (2006.01)
  *G06T 7/00* (2017.01)
(58) Field of Classification Search
  CPC ............... A61B 5/0051; G01R 33/341; G01R 33/56358; G01R 33/5673; G06T 7/0012
  USPC ........................................... 600/410
  See application file for complete search history.

(56) References Cited

U.S. PATENT DOCUMENTS

| | | | |
|---|---|---|---|
| 2011/0166484 A1 | 7/2011 | Virta | |
| 2012/0068699 A1* | 3/2012 | Horkay | A61B 5/415 422/547 |
| 2013/0303882 A1* | 11/2013 | Kolipaka | G01R 33/56358 600/415 |
| 2015/0192653 A1* | 7/2015 | Sharif | A61B 5/0044 600/420 |
| 2015/0309140 A1* | 10/2015 | Trzasko | G01R 33/56358 324/309 |
| 2016/0007968 A1* | 1/2016 | Sinkus | A61B 5/0051 600/410 |
| 2016/0030009 A1* | 2/2016 | Hoelscher | A61B 8/481 600/458 |
| 2017/0246482 A1* | 8/2017 | Hananel | A61B 17/2251 |

OTHER PUBLICATIONS

Klucinec, B. (1996). The effectiveness of the aquaflex gel pad in the transmission of acoustic energy. Journal of athletic training, 31(4), 313. (Year: 1996).*

"Siemens. Magnetic Resonance Imaging. (Dec. 2012) [retrieved on Jun. 27, 2017, https://w5.siemens.com/web/ua/ru/medecine/detection_diagnosis/magnetic_resonans/035-15-MRI-scaners/Documents/mri-magnetom-family_brochure-00289718.pdf] p. 6-8, 13, 15-16, PCT search report dated Jul. 19, 2017".

"International Application Serial No. PCT/US2017/022911, Written Opinion dated Jul. 19, 2017, PCT report opinion dated Jul. 19, 2017", 10 pgs.

"Gualda et al. SPIM-fluid: open source light-sheet based platform for high-throughput imaging. Biomed Opt Express (Nov. 1, 2015} vol. 6, No. 11, pp. 4447-4456, p. 4448 para 2-3, p. 4450, para 2, PCT search report dated Jul. 19, 2017".

"International Application Serial No. PCT/US2017/022911, International Search Report dated Jul. 19, 2017, PCT search report dated Jul. 19, 2019", 4 pgs.

Hornak, J. article entitled "The Basics of MRI," http://www.cis.rit.edu/htbooks/mri/inside.htm.

Klucinec, B., "The Effectiveness of the Aquaflex Gel Pad in the Transmission of Acoustic Energy," Journal of Athletic Training, 1996:31(4):313-317.

* cited by examiner

SYSTEM AND METHOD FOR MAGNETIC RESONANCE ELASTOGRAPHY

CROSS-REFERENCE TO RELATED APPLICATIONS

This application claims priority under 35 U.S.C. § 119(e) to U.S. Provisional Application Ser. No. 62/310,667, entitled "System and Method for MR Elastography," filed Mar. 18, 2016, which is herein incorporated by reference in its entirety.

BACKGROUND

Field

The described embodiments relate generally to medical imaging, more specifically to Magnetic Resonance imaging (MRI), ultrasonic imaging (e.g. ultrasound), and Magnetic Resonance Spectral Imaging (MRSI), and more specifically to techniques for scanning, capturing, searching, aggregating and processing imaging data, and providing medical information services and medical services based on the captured and aggregated imaging data.

Related Art

Generally, most tissue samples in hospitals are evaluated by a medical specialist and then destroyed, with a few symptomatic samples being preserved for medical research purposes. Presently, there are no large standardized datasets that contain routinely symptomatic and asymptomatic tissue samples for comparison and improvement of medical diagnoses.

SUMMARY

Trends in connectivity and in medical imaging technology are resulting in dramatic changes in people's lives. For example, the Internet now allows doctors, researchers, and data scientists to access vast amounts of anonymized information, as well as the ability to interact with individual patients and provide diagnoses around the world. This remote electronic capability has improved the quality of healthcare and reduced costs. Similarly, the increasingly powerful computing and communication capabilities of cloud computing and infrastructure as a service (IAAS) product offerings from companies such as Amazon Web Services and Cloudera combined with portable electronic devices (such as smartphones and tablets), as well as a large and growing set of applications, are accelerating these improvements, and the ability to leverage medical information to perform a wide variety of diagnoses.

As imaging technology improves, both higher resolution information as well as new types of information can be measured, which drives an ever-increasing trend of specialization in radiology. The disclosure provided herein includes systems and methods for magnetic resonance Elastography of biological lifeforms and of biological samples (including, e.g., fresh "wet" tissue samples, frozen samples, and formalin fixed-paraffin embedded (FFPE) samples) to create a large database of symptomatic and asymptomatic Magnetic Resonance signature data for use in automatically detecting anomalies and healthy tissue, performing more detailed scans of detected anomalies, and either automatically classifying between anomalies and healthy tissue using a software algorithm, and/or providing the images to radiologists who specialize in the type of tissue or anomaly detected for verification and/or identification. The tissue sample signatures can be applied to better detect anomalies on an individual basis. What is normal in one body might be slightly different than what is normal in another body, and clusters of tissue samples reflecting various shades of normal can help classify tissue. Finally, the amount of data that can be captured about each sample is much larger than the amount of data that can be processed by a single pathologist or radiologist or even a team of radiologists and pathologists. With the systems and methods provided herein, hospitals and research institutions would be able to catalogue and index all their tissue samples and contribute to building a large database of signatures of indexed tissues covering both symptomatic and asymptomatic tissue samples.

For a few decades, MRI technology has been the imaging modality of choice for soft tissue and morphological studies. As field strengths have continued to rise, the technical feasibility of MR Spectroscopy has been demonstrated, opening the possibility for MRSI to do both morphological and functional imaging in parallel. The technology facilitates high spatial and spectral resolution sample indexing and can also incorporate capturing signatures of Magnetic Resonance (MR) which can measure quantitative profiles of specific tissues of both symptomatic and asymptomatic tissue, such as tissue samples from biopsies, whether benign or non-benign, and can detect known healthy (i.e., whitelisted tissue) and known anomalous tissue (i.e., blacklisted tissue) and classify unknown tissue in a grey zone (i.e., greylisted tissue), which can be marked for inspection by other MR spectra, additional related biopsies, inspection by a radiologist, a pathologist, or other analysis as may be determined to be necessary.

In some embodiments, scans can also include MR Elastography, which measures the stiffness of tissue by sending mechanical waves through the tissue with an MRI technique including sending shear waves into the tissue, acquiring images of the propagation of the shear waves, and processing the images of the shear waves to produce a quantitative mapping of the tissue stiffness, which are known in the literature as elastograms.

Described herein are systems and methods for performing MR Elastography (using an ultrasonic wave generator) on both biological lifeforms and tissue samples. Another unique aspect of this system is that it is optimized to screen both symptomatic and asymptomatic tissue samples, as it is just as important to recognize healthy tissue as it is to recognize pathology.

In this model, each voxel in the sample in the MR scan has multi-dimensional data on the volumetric density of certain chemical signatures and atomic nuclei. This system can be aware of the region of the body or the source of the sample in which a sample originated and can use that knowledge to further optimize the configuration to best collect information about the sample. Additionally, the system can be used to scan multiple samples from the same subject, or different subjects can be scanned simultaneously, if increased throughput is needed.

On aspect of the present disclosure is directed to an apparatus for use in a magnetic resonance (MR) system for capturing an MR Elastography measurement of a biological lifeform. In some embodiments, the apparatus includes a platform; a gel pad on a surface of the platform; and a sensor array. In some embodiments, the sensor array includes at least one ultrasound transducer, and at least one radiofrequency (RF) transmitter and receiver coil. In some embodiments, the sensor array is at least partially embedded within the gel pad and the gel pad is configured to provide mechanical impedance matching between the at least one ultrasound transducer and the biological lifeform.

In some embodiments, the gel pad includes a surface feature in a location where the gel pad contacts the sensor array. In some such embodiments, the surface feature is one of: a divot, a rib, a groove, a depression, an indentation, and an impression.

In some embodiments, the platform includes an electromagnetically permeable material. In some such embodiments, the electromagnetically permeable material includes one or more of: Teflon, concrete, wood, sapphire, and poly-dimethyl siloxane.

In some embodiments, the gel pad further includes a fluid on a surface of the gel pad, such that the biological lifeform is at least partially ensheathed in the fluid, and the fluid is configured to transport the biological lifeform across the sensor array. In some such embodiments, the fluid comprises one or more of: saline, an ultrasound gel, and a mineral oil.

In some embodiments, the apparatus further includes a fluid source on a first end of the platform and a fluid sink on a second end of the platform. In some such embodiments, a fluid discharged from the fluid source at least partially ensheathes the biological lifeform and moves the biological lifeform across the sensor array to the fluid sink.

In some embodiments, the gel pad is adapted to function as an imaging phantom.

In some embodiments, a composition of the gel pad comprises a substance with a known proton density.

In some embodiments, a composition of the gel pad comprises a contrast agent.

In some embodiments, the sensor array further includes one or more of: an optical sensor, an infrared sensor, a conductance sensor, a movement sensor, a fiber optic sensor, a photoplethysmogram sensor, a piezoelectric sensor, and an electrocardiogram sensor.

In some embodiments, the biological lifeform is one of: a tissue sample and a patient.

In some embodiments, the MR system is one of: a closed bore system and an open bore system.

In some embodiments, the platform is movable. In some embodiments, the platform is a movable through an open bore or parallel plate MR System.

In some embodiments, the gel pad is configured to increase a distance between the at least one ultrasound transducer and the biological lifeform.

Another aspect of the present disclosure is directed to a system for capturing an MR Elastography measurement of a biological lifeform. In some embodiments, the system includes: an MR system including: an ultrasonic wave generator, an interface circuit, and a computing device, such that the ultrasonic wave generator is configured to generate one or more shear waves in the biological lifeform; and a platform, a gel pad on a surface of the platform, and a sensor array. In some embodiments, the sensor array includes at least one ultrasound transducer, and at least one RF transmitter and receiver coil. Further, in some embodiments, the sensor array is at least partially embedded within the gel pad and the gel pad is configured to provide mechanical impedance matching between the at least one ultrasound transducer and the biological lifeform. In some embodiments, the interface circuit is configured to communicatively couple the sensor array and the ultrasonic wave generator to the computing device such that the computing device is configured to generate a quantitative map of a tissue stiffness of the biological lifeform.

In some embodiments, the platform is movable through the MR system. In some such embodiments, the MR system is one of: a closed bore system and an open bore system.

In some embodiments, the gel pad further includes a fluid on a surface of the gel pad, such that the biological lifeform is at least partially ensheathed in the fluid, and the fluid is configured to transport the biological lifeform across the sensor array.

In some embodiments, the system further includes a fluid source on a first end of the platform and a fluid sink on a second end of the platform, such that a fluid discharged from the fluid source at least partially ensheathes the biological lifeform and moves the biological lifeform across the sensor array to the fluid sink.

In some embodiments, the system further includes a program module stored in the computing device, such that the program module includes instructions for performing the MR Elastography measurement on the biological lifeform.

In some embodiments, the interface circuit communicates wirelessly with the sensor array and the ultrasonic wave generator.

Another aspect of the present disclosure is directed to a method for capturing an MR Elastography measurement of a biological lifeform. In some embodiments, the method includes: providing a platform, a gel pad on a surface of the platform, and a sensor array, such that the sensor array includes: at least one ultrasound transducer, and at least one RF transmitter and receiver coil, and the sensor array is at least partially embedded within the gel pad and the gel pad is configured to provide mechanical impedance matching between the at least one ultrasound transducer and the biological lifeform; and generating one or more shear waves in the biological lifeform; acquiring one or more images of a propagation of the one or more shear waves; and processing the one or more images to produce a quantitative map of a tissue stiffness of the biological lifeform.

In some embodiments, the method further includes identifying an anomaly in the biological lifeform based, at least in part, on the quantitative map. In some such embodiments, the method further includes classifying the anomaly as one of: healthy, unhealthy, benign, and malignant.

In some embodiments, the method further includes altering a water content of the gel pad before or during capture of the MR Elastography measurement.

In some embodiments, the method further includes applying a fluid to a surface of the gel pad, such that the biological lifeform is at least partly ensheathed in the fluid.

In some embodiments, the method further includes applying a negative pressure or a positive pressure to the gel pad to move the biological lifeform suspended in the fluid across the at least one ultrasound transducer.

In some embodiments, generating the one or more shear waves is performed by an ultrasonic wave generator.

In some embodiments, acquiring the one or more images is performed by the at least one ultrasound transducer.

In some embodiments, processing the one or more images is performed by an interface circuit and a program module stored in a computing device, such that the interface circuit couples the at least one ultrasound transducer to the computing device.

In some embodiments, the method further includes altering a composition of the gel pad with one or more of: a contrast agent, a substance with a known T1 and T2, and a known proton density.

In some embodiments, the method further includes altering one or more of: an elasticity and a viscosity of the gel pad to alter a surface area of the gel pad in contact with the biological lifeform.

In some embodiments, the sensor array further includes one or more of: an optical sensor, an infrared sensor, a conductance sensor, a piezoelectric sensor, a movement sensor, a fiber optic sensor, a photoplethysmogram sensor, and an electrocardiogram sensor. In some embodiments, the method further includes monitoring a pulse of the biological lifeform using the sensor array. In some embodiments, the method further includes measuring one or more of: a weight, a volume, and a density of the biological lifeform using the sensor array.

Some embodiments may include an ultrasonic wave generator, and the program module may include instructions for performing MR Elastography on the sample. In some embodiments, the MR scanner is a bore scanner, and the ultrasonic wave generator generates waves at the ends of the bore of the MR scanner.

The preceding summary is provided as an overview of some exemplary embodiments and to provide a basic understanding of aspects of the subject matter described herein. Accordingly, the above-described features are merely examples and should not be construed as narrowing the scope or spirit of the subject matter described herein in any way. Other features, aspects, and advantages of the subject matter described herein will become apparent from the following Detailed Description, Figures, and Claims.

DETAILED DESCRIPTION

The disclosure provided herein includes a system and methods for magnetic resonance (MR) Elastography of biological lifeforms and of biological samples (including fresh "wet" tissue samples, frozen samples, and formalin fixed-paraffin embedded (FFPE) samples) to create a large database of symptomatic and asymptomatic MR Field Invariant Signature data for use in automatically detecting anomalies and healthy tissue, performing more detailed scans of detected anomalies, and either automatically classifying between anomalies and healthy tissue using a software algorithm and/or providing the images to radiologists who specialize in the type of tissue or anomaly detected for verification and/or identification, and especially relating to MR Elastography (MRE).

Moreover, in the discussion that follows, 'MRE' should be understood to include measuring the stiffness of a sample using MRI by sending mechanical waves (such as sheer waves) through a sample, acquiring images of the propagation of the shear waves, and processing the images of the shear waves to produce a quantitative mapping of the sample stiffness (which are sometimes referred to as 'elastograms') and/or mechanical properties (such as rigidity, density, tensile strength, etc.).

In some embodiments, the one or more MRE images may be derived from a tensor field map. The tensor field mapping process may include applying a polarizing field and an excitation sequence to the sample and measure a corresponding response or physical phenomenon of the sample. Then, the system may iteratively converge the measurements with a forward model that predicts the physical phenomenon based on the parameters.

By facilitating determination of the parameters in voxels in the sample (which is sometimes referred to as 'tensor field mapping,' because the parameters in the voxels can be represented by a hybrid tensor as opposed to a true tensor for a vector field), this characterization technique may reduce the scan or measurement time. Therefore, the characterization technique may significantly reduce the cost of characterizing the sample by increasing throughput. Moreover, in embodiments where the sample is a patient, the reduced scan time may improve the user experience, such as by reducing the amount of time people spend in the confining environment of a magnet bore in an MR scanner. In addition, the one or more parameters and the forward model may facilitate quantitative analysis of the measurements and, thus, may improve the accuracy of the scans, thereby reducing errors, and improving the health and well-being of people.

Figure 7:
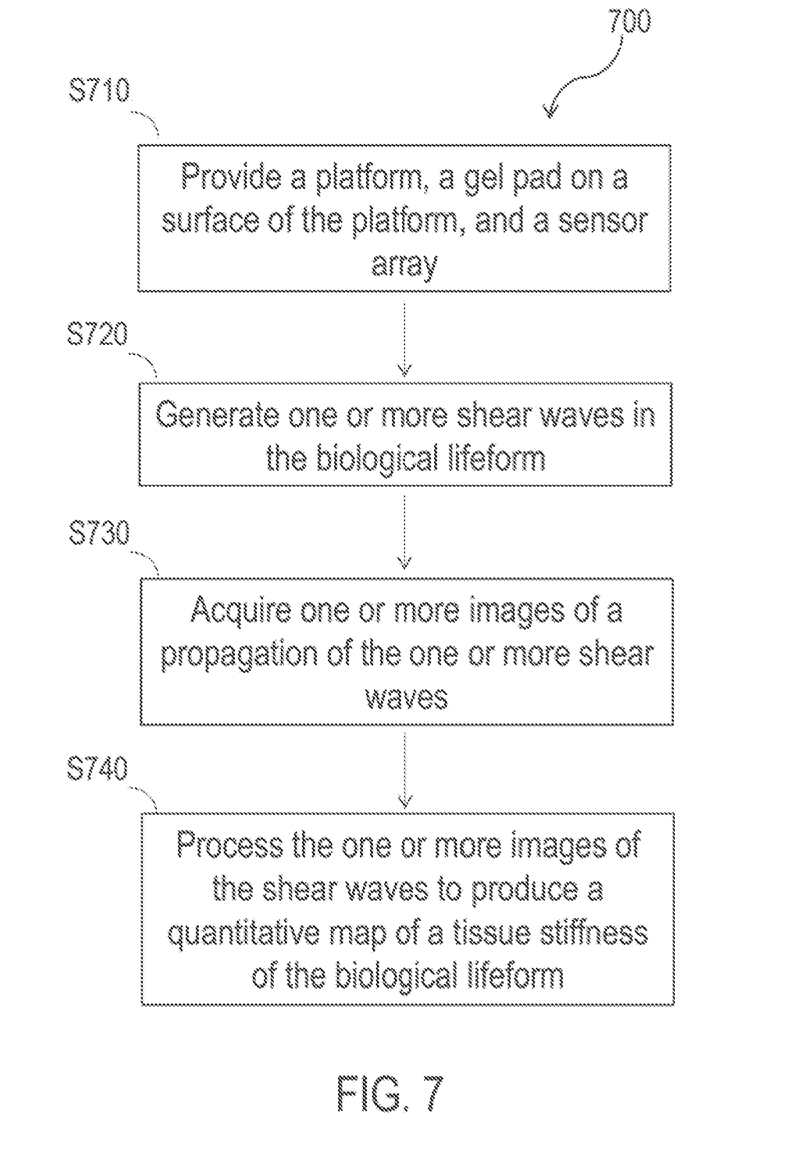
FIG. 7 depicts a flow chart of one embodiment of a method for capturing an MR Elastography measurement of a biological lifeform.

As described elsewhere herein, a scan may also include MR Elastography, which measures the stiffness of tissue. As shown in FIG. 7, a method 700 for capturing an MR Elastography measurement of a biological lifeform may include: generating one or more shear waves in the biological lifeform 720, for example by sending mechanical waves through the tissue with an MRI technique; acquiring one or more images of a propagation of the one or more shear waves 730, and processing the one or more images of the shear waves to produce a quantitative map of a tissue stiffness (i.e., elastograms) of the biological lifeform 740. In some embodiments, the method 700 further includes: providing a platform, a gel pad on a surface of the platform, and a sensor array 710, as will be described in further detail elsewhere herein.

As medical imaging and other medical diagnostic technology improves, both higher resolution information as well as new types of information can be measured quantitatively which drives an ever-increasing trend of specialization in radiology and other medical diagnostic techniques. The disclosure provided herein includes a system and methods for using a combination of MR techniques including but not limited to MR signature capture, Morphology scanning, Elastography, Spectroscopy, Thermometry, Diffusion Tensor mapping, and Tensor Field Mapping. This capability can help diagnostics determine which parts of tissue in vivo may require more detailed scans of detected anomalies by either algorithmically classifying anomalies as healthy/unhealthy tissue and/or providing the images to radiologists who specialize in the type of tissue or anomaly detected for verification and/or identification. Finally, the amount of data that can be captured about each sample is much larger than the amount of data that can be processed by a single pathologist or radiologist or even a team of radiologists and pathologists.

Scanning of tissue samples can be performed by many types of MR scanners (including cryo and non-cryo MRI systems, low field imaging systems that use lower field strength magnets), as well as other types of medical imaging devices, including ultrasounds and computerized tomography (CT). Images can be individual 2-dimensional images, such as MRI scans, or X-rays or CT scans, or can include 3-D models determined from voxels in MRI scans and/or other image processing techniques, and can include animations of a body or a portion of a body over time (e.g. over weeks, months or years, or during a surgery). Additionally, MR Signature detection can be used to scan tissue samples. Tissue sample scans can be tied to optical, thermal sensors, and scans can also include one or more spectra, one or more voxel sizes, one or more MR modalities, one or more $B_0$ or $B_1$ field strengths, or one or more ultrasound techniques. Any pulse sequence can be used, and while certain pulse sequences can have effects, the techniques described in this disclosure are not dependent on the use of any particular pulse sequence.

Figure 1:
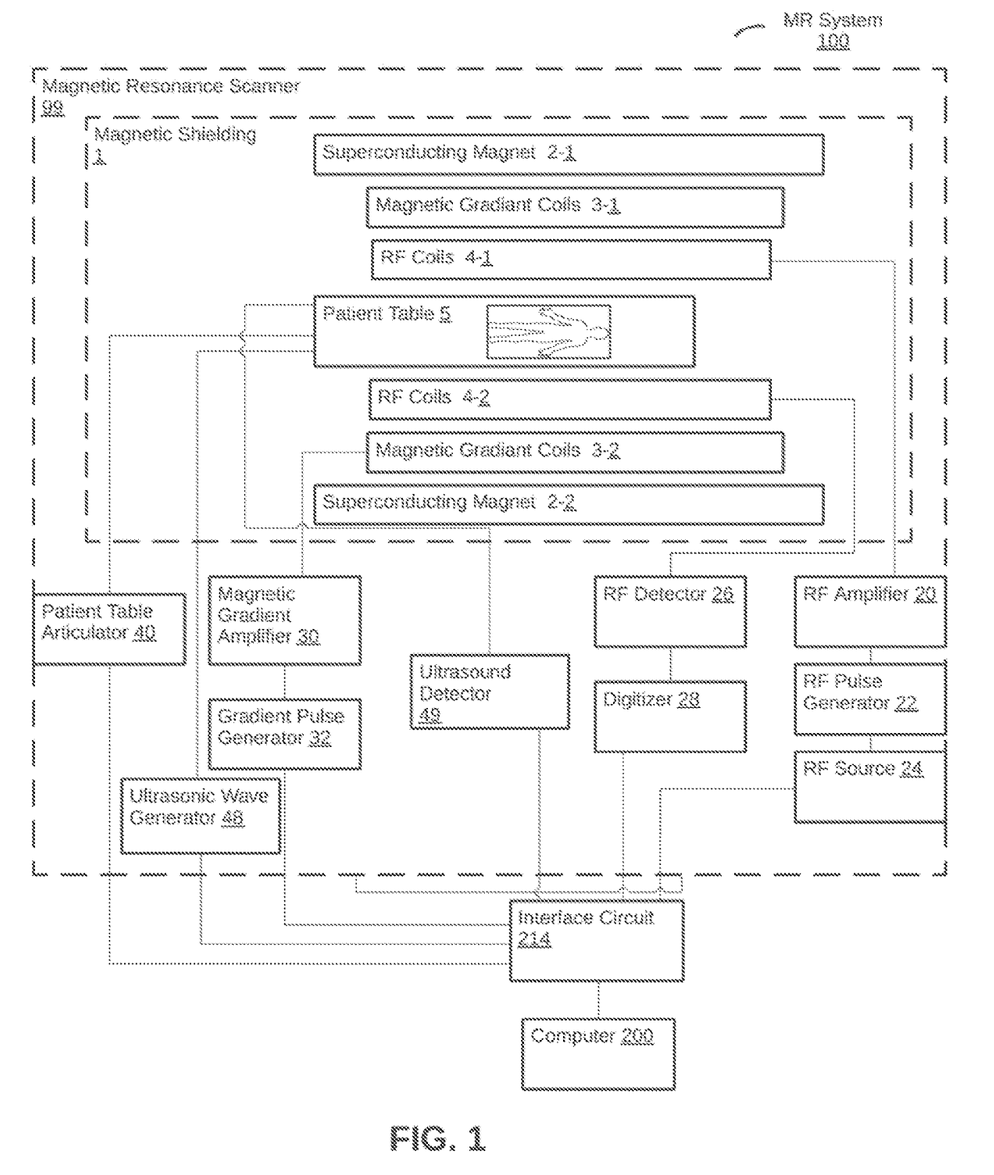
FIG. 1 is a block diagram illustrating a magnetic resonance scanner equipped with an ultrasonic wave generator adapted for humans or animals.
Figure 2:
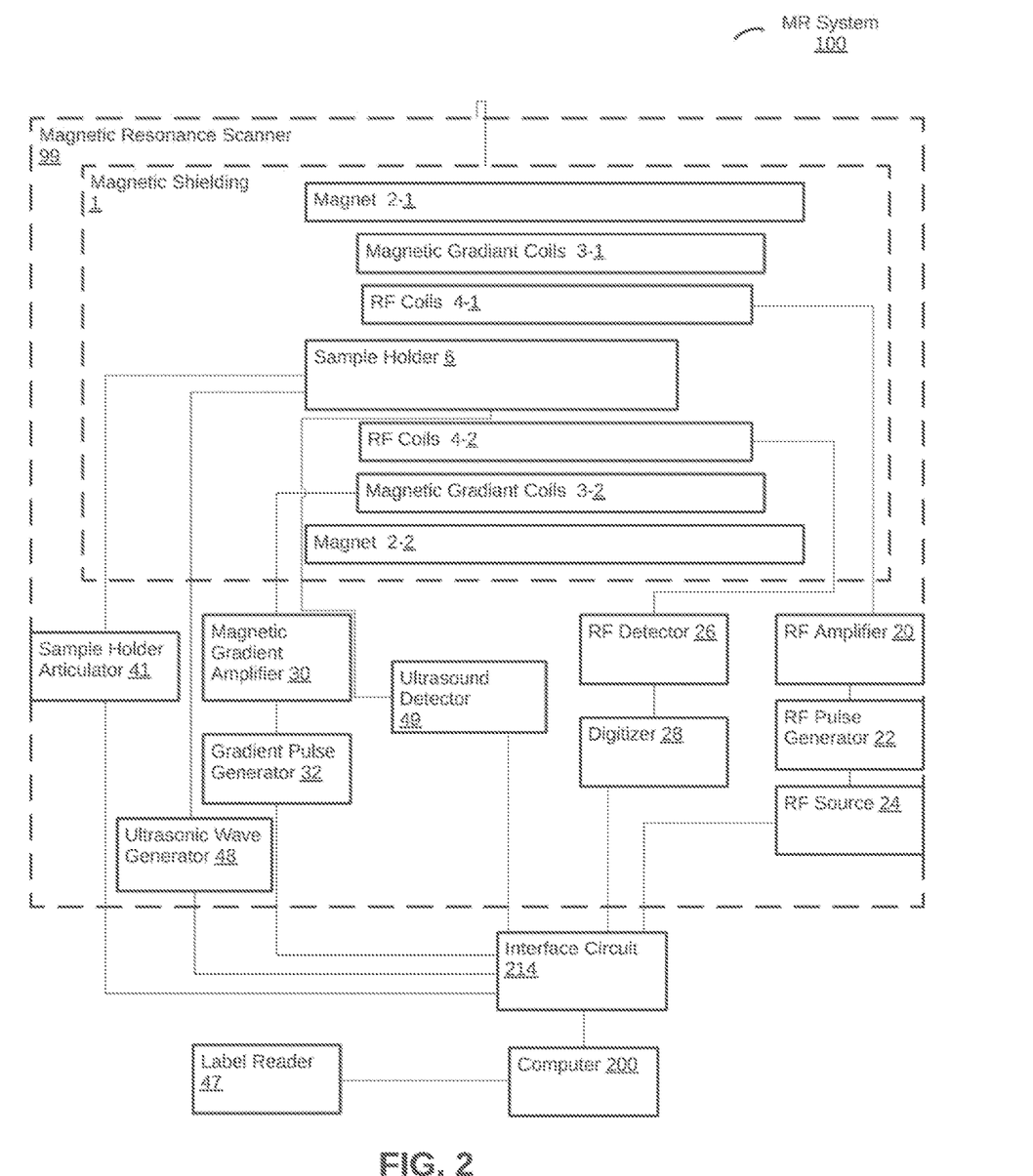
FIG. 2 is a block diagram illustrating a magnetic resonance scanner equipped with an ultrasonic wave generator adapted for biological samples.

By way of introduction and definition, we now describe the basic functionality for a standard MR system 100. In a first group of embodiments, as shown in FIGS. 1-2, an MR system 100 includes a Magnetic Resonance (MR) Scanner 99, which includes magnetic shielding 1, a magnet 2, magnetic gradient coils 3, RF coils 4, a patient table 5 (or a sample holder 6) an RF amplifier 20, an RF pulse generator 22, an RF source 24, an RF detector 26, a digitizer 28, a magnetic gradient amplifier 30, a gradient pulse generator 32, a patient table articulator 40 (or a sample holder articulator 41), an ultrasonic wave generator 48, and an ultrasound detector 49, all connected through an interface circuit 214 to a computer 200, which can control the components of the MR scanner via control mechanisms, program modules, processor implemented methods, and the like. These components of the MR scanner 99 are described briefly below, but more detail is available in Chapter 9 of "The Basics of MRI" by Dr. Joseph P. Hornak, the entire disclosure of which is incorporated herein by reference.

The MR system 99 as shown in FIG. 1 may be a closed bore or an open bore system (i.e., parallel plate system). The magnet 2 (shown as a cutaway in 2 portions 2-2, and 2-1) may be either closed bore or open bore. An open bore system may utilize a magnetic field between two plates, and may be low field (e.g. less than 0.1 Tesla) strong ferromagnetic magnets (approximately 0.5 T) or high field (e.g., over 1 Tesla) depending on the imaging technology to be used for diagnosis. A closed bore system may include a toroid shaped (or in layman's terms a donut shaped) magnet and the patient or sample may be moved through the hole in the center of the toroid (thus exposing the patient or the sample to the strong magnetic field), and systems are generally horizontal (known as horizontal bore) moving the sample horizontally through the field, but may also be vertically oriented. An open bore system includes a gap between two plates, and the patient may be moved between the plates, and exposed to a strong magnetic field between the plates. The MR system 99 may be applied to MR scanners that scan patients and/or samples in various positions, including multiple angles, orientations and perspectives.

The magnet 2 may be a superconducting magnet, and superconducting magnets are the most common types of magnets used. However, any suitably strong magnet may be used, and configurations of magnets 2 that may work at room temperatures are known in the art. Magnets down to 0.001 T may be used at room temperature in open bore configurations, and may have the added effect of imaging metallic objects due to their low field. The magnet 2 is most commonly closed bore, and made from a coil of Niobium Titanium (NbTi) wire or Niobium Tin ($Nb_3Sn$) wire, both Type II semiconductors, and the amount of wire used may typically be several miles. The wire coil is kept at a superconducting temperature of 4.2 Kelvin by insulating it in liquid Helium (He). In some systems, the liquid helium is insulated and thermally buffered by liquid nitrogen (N) to prevent boiling off the He, and in some systems a refrigerated or otherwise cooled dewar is used, to contain the liquid He for periods of up to 3-4 years. There are currently efforts researching using liquid hydrogen since there is finite supply of helium on earth, different coolants may be used to cool the coils and rooms. The purpose of the superconducting magnet 2 in the MR system is to create a very strong magnetic field, referred to hereafter as $B_0$ (B-nought), and align the spins of nuclei when they are exposed to the strong magnetic field. The magnet 2 may be a smaller bore magnet from 1 cm to 10 cm or 5 cm to 30 cm, but may also be any suitable size. In some embodiments, smaller magnets may be used for processing medical samples and biopsies. For example, with a smaller magnet 2, it becomes possible for the entire MR scanner 99, including the computer 200, to fit on a wheeled cart and be wheeled between rooms or departments in a medical facility such as a clinic, hospital, or research institution.

The magnetic shielding 1 may be composed of steel plates, or it may be composed of silicon steel in the form of metal sheets, with the latter being easier to work with. The shielding 1 may be placed all around a room, fully covering walls, floors and ceilings, with the main purpose being to attenuate the field strength to below 5-gauss as per FDA recommended guidelines. Special doors and doorframe seals may be used to further reduce the field that can leak out of the room. Alternatively, some magnets include shielding on the magnet to reduce the fringe field, with known examples in operation in the field dropping to 0.5 mT at a range of 4 meters from the magnet. This reduces the need for magnetic shielding, and depending on the site, may eliminate the need for magnetic shielding entirely. The shielding on the magnet is achieved by including a second set of windings (also superconducting) operating with opposite current flow outside the main superconducting windings to reduce the fringe field by canceling out the magnetic field.

The magnetic shielding 1 may also function as a chamber and be a sealed chamber, such that an Ultrasound detector 49, as shown in FIGS. 1-2, may be coupled to a vacuum pump and used to remove air from the chamber, (e.g. create a vacuum chamber), or alternatively the Ultrasound detector 49 may be coupled to a gas tank and the chamber may be flooded with an inert gas, such as Xenon to improve MR imaging quality, and the inert gas may be polarized.

The magnetic gradient coils 3 typically operate at room temperature and function to produce gradients in $B_0$. Typically, in horizontal bore systems, using standard magnetic resonance coordinates, a gradient in $B_0$ in the Z direction is achieved with an anti-Helmholtz coil, with current in each coil adding or subtracting to $B_0$ to achieve a gradient. The X and Y gradients may be created by a pair of figure eight coils, creating gradients along their respective axes. Gradient coil strengths are typically 100 mT/m and have fast switching times, also known as slew rates of 150 mT/m/ms, enabling 0.7 mm slice thickness and 0.1 mm voxel resolution in 3D imaging. In the U.S., slew rate limits are currently set at 200 T/m/s, with higher slew rates causing nerve stimulation. However, recent research has shown that, at frequencies above approximately 100 kHz (corresponding to a rise-time below 10 microseconds, and corresponding to a slew rate of 160,000 T/m/s), no nerve stimulation occurred, even with varying pulse shapes. Stronger magnets (7 Tesla for example) provide improved 3-dimensional imaging measurements down to 60 micrometers in isometric voxel sizes.

The magnetic gradient amplifier 30 functions to increase the power of the gradient pulses to a level suitable for driving the gradient coils. The magnetic gradient pulse generator 32 functions to produce the shape and amplitude of the gradient field in each of the 3 gradient fields (X, Y, and Z in standard MRI coordinates). The magnetic gradient amplifier 30 and the magnetic gradient pulse generator 32 are both controlled by the computer 200 via an interface circuit 214.

The RF coils 4 create a $B_1$ field that rotates the net magnetization in a pulse sequence. They also detect transverse magnetization as it processes in the XY plane, RF coils 4 may transmit only, receive only, or may function as both transmitter and receiver. The RF coils 4 need to be oriented such that the $B_1$ field is perpendicular to the $B_0$ field. The RF coils 4 may be tuned to the Larmor frequency (e.g. resonant frequency of a nuclei being imaged at $B_0$) by adjusting the capacitor or inductor, but generally varying capacity capacitors and inductors are used (matching and tuning capacitors). Any number or type of RF coils may be used including an Alderman-Grant Coil, Bird Cage, Butterfly Coil, Dome Resonator, Gradiometer, Implantable Coil, Inside Out/ Schlumberger Coil, Intravascular Coil, Ladder Coil, Litz Coil, Loop-Gap Resonator Coil, Loop-Stick-Coil, Meanderline Coil, Mouse Coil, Multi-Turn Solenoid Coil, Phased Array Coil, Phased Array Volume Coil, Ribbonator Coil, Saddle Coil, Scroll Coil, Single Turn Solenoid Coil, Spiral Coil, Superconducting Coil, Transmission line coil, Truncated Spiral Coil, and 3-Axis coil. Birdcage coils are typically used for volume, single turn solenoid coils are typically used for extremities, and surface coils (receive only) are commonly used for body imaging because they give a good Signal to Noise Ratio (SNR) of tissues and samples adjacent to the coil. Additionally, wideband RF coil transmitters may be used to excite multiple spectra simultaneously, and may be used with wideband RF receiving coils.

The coils may include thermal imaging sensors, which may include a forward-looking infrared (FLIR) sensor. The additional sensors may be attached modularly (either snapped together in concentric shells, or snapped on additions, assembled with interlocking interfaces, and may communicate with each other via wireless or wired connections. As one or more sensors pass regulatory approval, they may graduate from research to commercial use and be added onto a coil for commercial applications.

Additionally, in one variation, surface coils may be controlled by software executing the scan plan (e.g., determining which body portions to scan at each time point; determining how to orient the slices and in what plane, etc.) such that certain modalities may be turned on and off in real-time as determined by analysis of the sample, e.g. to take an MR Elastography measurement of the anomaly, a thermal image of the sample, or the surrounding region. In this example, the coils may be constructed to include multiple sensors and data collection equipment to be used for specialized anomaly detection. For example, the MR RF coils may be optimized for parallel collection of data by MR Thermometry, MR Field Invariant Signature Detection, MR Spectroscopy, MR Elastography, Multi-nuclear imaging of two or more nuclei ($^1H$, $^{23}Na$, $^{31}P$, $^{13}C$, $^{19}F$, $^{39}K$, $^{43}Ca$), Diffusion Tensor Imaging, or N-channel scanning.

In one embodiment, the readings from coils may be digitized within or just outside of the coil assembly and transmitted wirelessly to a computer 200. Wireless transmission avoids messy cable tangling without creating significant RF noise in the frequencies of interest. Wireless transmission may include transmitting data to the computer 200 at lower or higher frequencies than the $\gamma B_0$ frequencies of the targeted nuclei in the MR field invariant signature detection, outside of the frequencies measured, and filtering inputs and outputs and noise artifacts.

The RF amplifier 20 increases the power of the RF pulses to be strong enough to drive the RF coils, typically increasing the power from mW to kW. The RF amplifier 20 receives signals from the RF pulse generator 22 and/or the RF source 24. The RF source 24 produces sinewaves of the desired frequencies (e.g. tuned for desired nuclei and $B_0$ field strength). The RF pulse generator 22 functions to shape the RF pulses from the RF source 24 into apodized sine pulses. The RF amplifier 20 and the RF pulse generator 22, and the RF source 24 are each controlled by the computer 200 via an interface circuit 214. Apodized sine pulses excite the spin states of the nuclei, which store the energy in an excited state, and the excited state decays and releases a pulse of RF energy to be captured in acquisition Many different pulse sequences may be used, including turbo field echo (TFE), fast field echo (FFE), susceptibility weighted imaging (SWE), short Tau inversion recovery (STIR; also called short $T_1$ inversion recovery—this is a fat suppression technique with an inversion time $TI=T_1 \ln(2)$ where the signal of fat is zero. This equates to approximately 140 ms at 1.5 T), Turbo Spin Echo (TSE), Fast Low Angle Shot (FLASH: a special kind of spin-echo sequence where larger tip angles give $T_1$ weighted images, smaller give more $T_2^*$ weighted images), Volumetric Interpolated Brain Examination (VIBE), magnetic pulse rapid gradient echo (MP RAGE), and Fluid Attenuation Inverted Recovery (FLAIR). Parallel Imaging Techniques such as sensitivity encoding (SENSE) and Array coil spatial sensitivity encoding (ASSET) are the most widely used parallel imaging methods (mSENSE from Siemens, ASSET from GE, SENSE from Philips, RAPID from Hitachi and SPEEDER from Toshiba) and involves four steps: generate coil sensitivity maps, acquire partial k-space MR data, reconstruct partial field of view images from each coil, and combine partial field of view images by matrix inversion. Additional second and third generation parallel imaging techniques like GRAPPA, Auto-Smash, VD-SMASH which are parallel imaging techniques to speed up MRI pulse sequences using K-space undersampling, and the acquisitions of the additional lines is also a form of calibration, as the coefficients of signals across coils may be determined from the measurements.

The RF detector 26 functions to capture the RF signals and perform the simplest form of NMR/MRI/MRSI/MR Signature Detection where the signal is received from the free induction decay of excited spin states, though it is possible to receive many more complex pulse sequences. The RF detector may be a linear analog detector or a quadrature analog detector. Linear analog detectors may capture signals along one vector in the coordinate space (e.g. $M_x$ or $M_y$) and a quadrature analog detector may capture signals along two vectors in the coordinate space (e.g. $M_x$ or $M_y$) simultaneously. The linear analog detector is typically a doubly balanced mixer, and the quadrature analog detector is typically a pair of double balanced mixers, a pair of filters, a pair of amplifiers and a 90-degree phase shifter In some embodiments, the RF detector coils may be tuned to receive one or more frequencies, depending on the spectra desired, either a wide-band receiver coil may be used, or a software based or hardware based tuner may be used to automatically tune at least one RF detector coil to receive one or more frequencies from a desired nuclei or molecule.

As shown in FIGS. 3A-4B, an apparatus for use in a MR system for capturing an MR Elastography measurement of a biological lifeform may include a platform 201. A platform 201 may include at least one embedded RF transmitter and receiver coil 210 in an electromagnetically permeable material 202. While separate reference numbers are used, it will be appreciated by one skilled in the art that the platform 201 of FIGS. 3A-4B may be the patient table 5 of FIG. 1 or the sample holder 6 of FIG. 2. It is contemplated and intended that any of or all the features described with reference to FIGS. 3A-4B may be found on or in the patient table 5 of FIG. 1 and sample holder 6 of FIG. 2. In one variation, the platform 201 may include one or more RF transmitter and receiver coils 210 embedded in Teflon, Concrete, Wood, Sapphire or another electromagnetically permeably material functioning as a surface of the platform 201. In another variation, the platform 201 may include, in addition to or instead of an electromagnetically permeable material, a padded material to improve patient comfort, such as an inert semi-rigid polymer like PDMS (poly-dimethyl siloxane). The platform 201 may be movable such that it may be mechanically actuated, moved through the bore of a magnet 2, or moved through a zero-field scanner. For example, as shown in FIG. 3B, the platform 201 may include a base 240 that is movable or robotically actuated, such that the base 240 moves the platform 201 through an MR system, for example a parallel plate or open bore MR system.

Figure 3A:
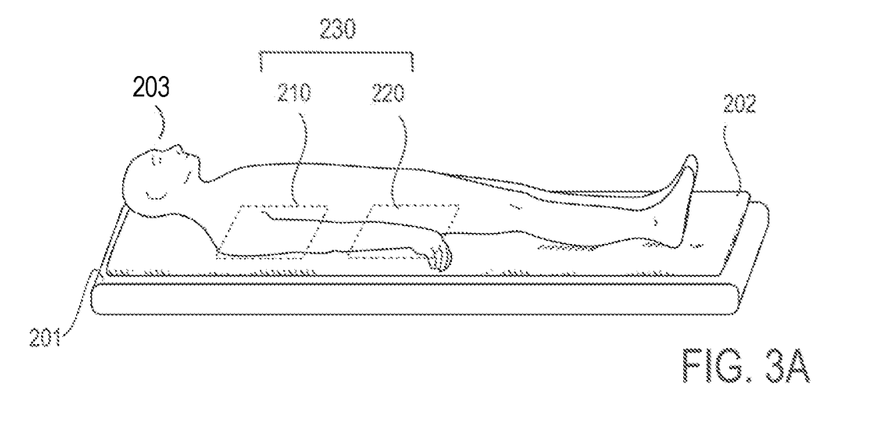
FIG. 3A is a diagram of a platform adapted for MR Elastography in accordance with an embodiment of the present disclosure.
Figure 3B:
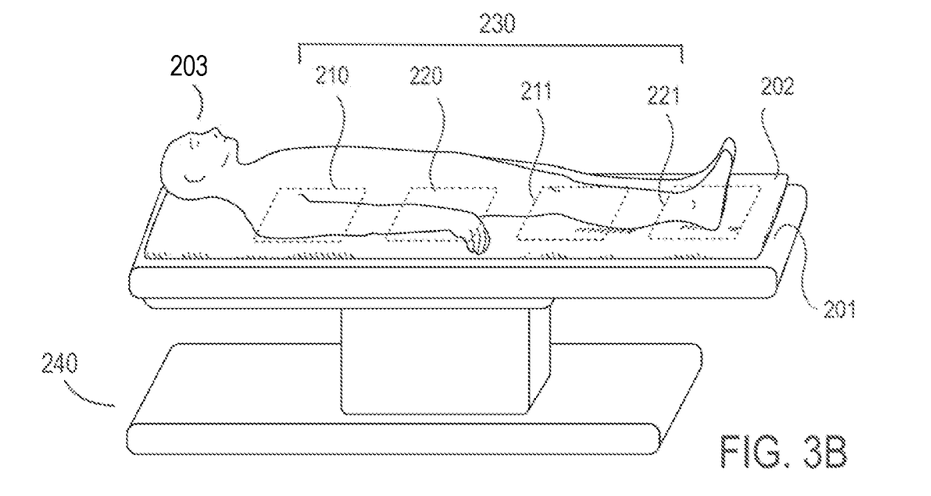
FIG. 3B is a diagram of a platform adapted for MR Elastography in accordance with an embodiment of the present disclosure.
Figure 6A:
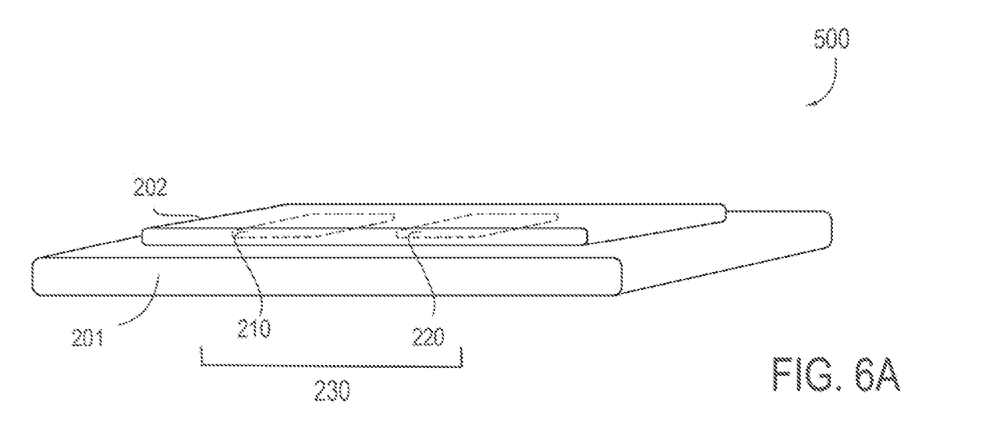
FIG. 6A is an assembled view of a sensor array embedded in a gel pad of a platform adapted for MR Elastography in accordance with an embodiment of the present disclosure.
Figure 6B:
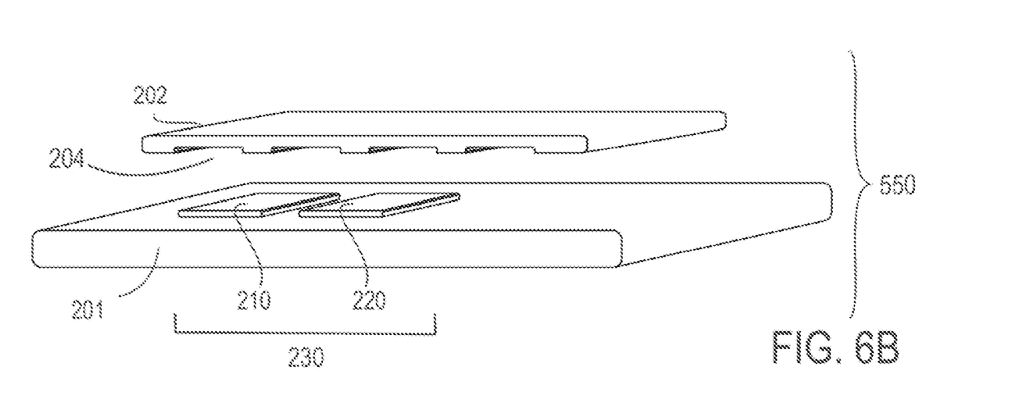
FIG. 6B is an exploded view of a sensor array embedded in a gel pad of a platform adapted for MR Elastography in accordance with an embodiment of the present disclosure.

In another variation, as shown in FIG. 3A, the surface of the platform 201 may be constructed from or include a gel pad 202. The gel pad 202 may function as a disposable ultrasound standoff (i.e., it increases the distance between the transducer face and the area of interest). In some embodiments, as shown in an assembled view 500 in FIG. 6A and an exploded view 550 in FIG. 6B, the gel pad 202 may include a sensor array 230 at least partially embedded therein. The gel pad 202 may include one or more surface features 204, for example divots, grooves, ribs, depressions, indentations, or impressions, that are configured to receive the sensor array 230, as shown in FIG. 6B. Returning to FIG. 3A, the sensor array 230 comprises at least one RF transmitter and receiver coil 210 configured to communicate with an MR system and at least one ultrasound transducer 220 (e.g., mechanical or piezoelectric). In some embodiments, as shown in FIG. 3B, the sensor array 230 comprises one or more or a plurality of RF transmitter and receiver coils 210, 211 and one or more or a plurality of ultrasound transducers 220, 221. The RF transmitter and receiver coil 210 may be embedded next to or adjacent to an ultrasound transducer 220 in the gel pad 202, as shown in FIGS. 6A-6B. The gel pad 202 may function as a transmitter of acoustic energy for ultrasound measurements, and such ultrasound measurements may also be performed during an MR scan in a process known as MR Elastography. The ultrasound transducer 220 may be capable of transmitting frequencies above the human hearing threshold, for example typical ultrasound refers to 20 kHz to 1 GHz.

In some embodiments, additional sensors may be embedded in the gel pad 202, including optical sensors, infrared sensors, conductance sensors, piezoelectric sensors, electrocardiogram sensors, electromyogram sensors, electroencephalogram sensors, photoplethysmogram sensors, movement sensors (e.g., an accelerometer, gyroscope), fiber optic sensors, or any other suitable sensors. For example, displacement of a surface of the gel pad 202 may be measured using one or more piezoelectric or movement sensors at least partially embedded in the gel pad 202. Such displacement measurements may be used to determine a volume, density, and/or weight of the biological lifeform. Further for example, a pulse, heart rate, heart rate variability, and/or stress level of a patient 203 resting on the gel pad 202 may be measured using one or more electrocardiogram sensors, movement sensors, or ultrasound transducers at least partially embedded in the gel pad 202. Such data may be used to synchronize a delivery of ultrasonic and radio waves to the patient 203. Monitoring the biological lifeform with one or more sensors may occur continuously, at a pre-determined time, in a pre-determined pattern, randomly, or on cue from an operator of the MR system.

The gel pad 202 may provide: comfort to a patient 203, thereby improving the patient experience; stability to a sample 199; and sterility or cleanliness by being disposable. A gel pad 202 may also provide better contact with bony surfaces of the body, open wounds, or other body surfaces that may be challenging for ultrasound probes to reach.

A number of materials will work for the transmission of the ultrasound energy into the biological lifeform. It is worth noting that the information captured in the elastogram may be noise tolerant, so the choice of material for the gel pad 202 or platform 201 need not be made solely based upon electromagnetic permeability or a material's ability to transfer ultrasonic energy. Rather, the choice of gel pad 202 material may be based, at least in part, on patient comfort, cost, ease of transport, manufacturability, disposability, and sanitation.

Disposability of the gel pad 202 may improve sanitary conditions, reduce the need for sterilization of surfaces, and reduce the risk of spreading diseases among patients and cross-contamination between samples in diagnostic and therapeutic ultrasound measurements. Gel and gel pads have been demonstrated in the literature to transmit more ultrasound energy than glycerin, mineral oil, or water.

In some embodiments, a composition of the gel pad 202 may include a synthetic resin, Aquaflex®, LiquiSonic®, rubber, urethane rubber, acrylic, or any other aqueous material. In another embodiment, the composition of the gel pad 202 may be adjusted to improve or reduce the conductance of ultrasonic waves and/or the fit to a patient's body.

In some embodiments, the adjustments may be performed by adding or removing water from a gel pad 202, either before or during a measurement, for example by increasing a water content during the manufacturing phase or removing water by applying heat to the gel pad.

In some embodiments, adjustments are performed by doping a gel pad 202 with a doping agent to improve conductance of ultrasonic waves or to differentiate the ultrasound gel or gel pad 202 from the patient 203. For example, a potassium salt may be added into a gel pad 202 to highlight a concentration of potassium in MR images or MR data capture of an MR Elastography measurement. Further, in another variation, the gel pad 202 may include a doping agent that conveys imaging phantom attributes to the gel pad 202. For example, the gel pad 202 may include a doping agent with a known Proton Density, T1 (i.e., longitudinal relaxation time) and T2 (i.e., transverse relaxation time), so that the gel pad 202, at least in part, functions as an imaging phantom. In still another variation, one or more contrast agents may be added to the gel pad 202, for example a gadolinium or gadolinium(III)-containing contrast agent, superparamagnetic iron oxide, superparamagnetic iron platinum, paramagnetic manganese, or a protein-based contrast agent. In some embodiments, the doping agent is at a concentration of 1-10 parts per million (ppm), 10-20 ppm, 20-30 ppm, 30-40 ppm, 40-50 ppm, 50-60 ppm, 60-70 ppm, 70-80 ppm, 80-90 ppm, or 90-100 ppm. In some embodiments, the doping agent has a concentration of 0-100 ppm, 100-250 ppm, or 250-500 ppm. In some embodiments, the doping agent comprises 0.0001% to 0.1%, 0.1% to 1%, or 1% to 5% of the gel pad 202. In another embodiment, the doping agent comprises 0.0001% to 10% of the gel pad 202. In another embodiment, the doping agent comprises 0.05% to 1% of the gel pad 202.

Further, in some variations, the doping agent is homogenously distributed in the gel pad 202. In other variations, the doping agent is distributed in the gel pad 202 in a pre-determined pattern or gradient. For example, different regions of the gel pad 202 may comprise different concentrations of the doping agent while some regions comprise no doping agent.

Additionally or alternatively, a viscosity or elasticity of the gel pad 202 may be adjusted to control or vary the degree to which the biological lifeform depresses the gel pad 202. For example, a less viscous or more elastic gel pad 202 increases the surface area of the gel pad 202 that contacts the biological lifeform, while a more viscous or less elastic gel pad 202 decreases the surface area of the gel pad 202 that contacts the biological lifeform.

The gel pad 202 may be manufactured with divots, ribs, or other surface features 204 to interface more tightly or intimately with the RF transmitter and receiver coil 210 and the ultrasound transducer 220, as shown in FIG. 6B. The gel pad 202 may be molded, laser cut, stamped, or manufactured in any other suitable fashion.

Figure 4A:
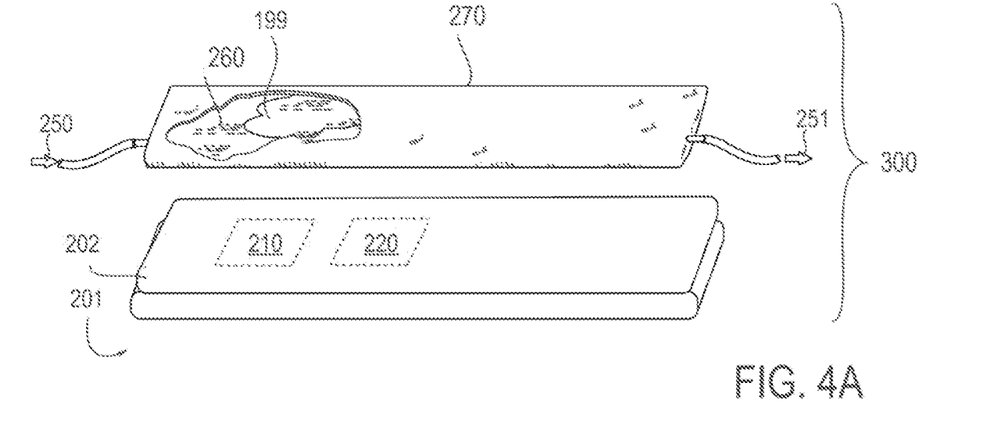
FIG. 4A is an exploded view of a platform adapted for MR Elastography in accordance with an embodiment of the present disclosure.
Figure 4B:
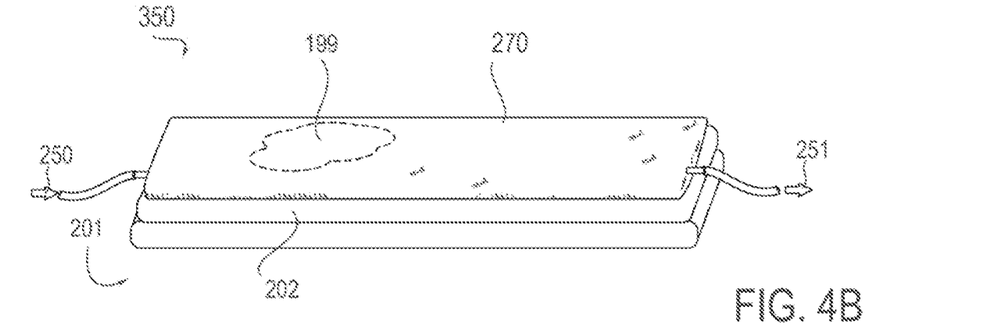
FIG. 4B is an assembled view of a platform adapted for MR Elastography in accordance with an embodiment of the present disclosure.
Figure 5A:
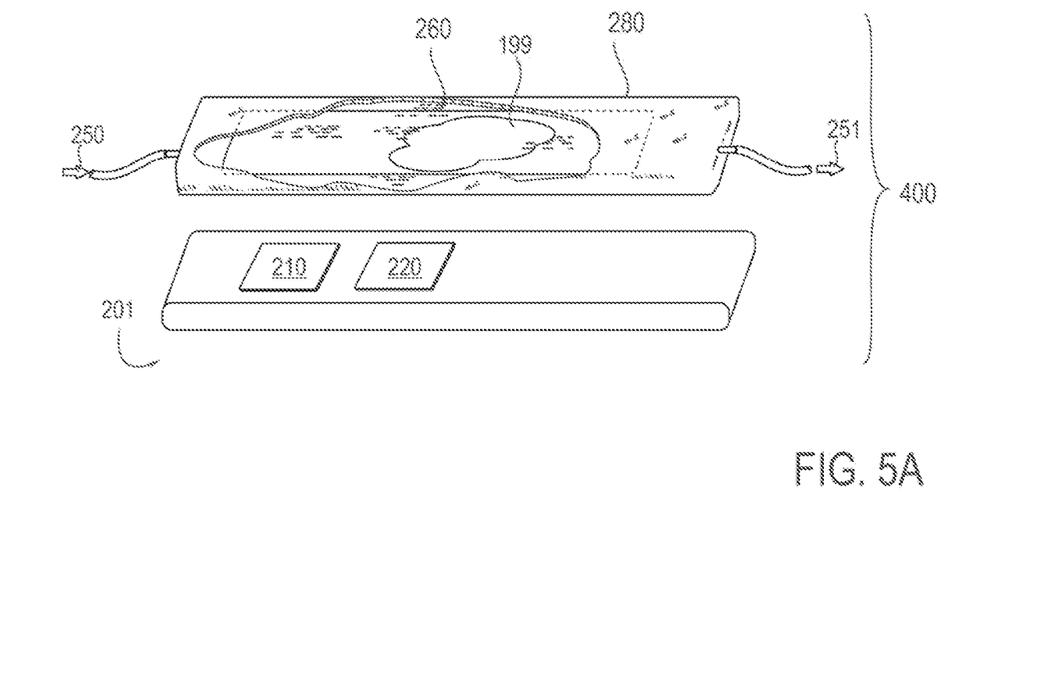
FIG. 5A is an exploded view of a flow cell adapted to use a fluid to sheath samples for MR Elastography in accordance with an embodiment of the present disclosure.
Figure 5B:
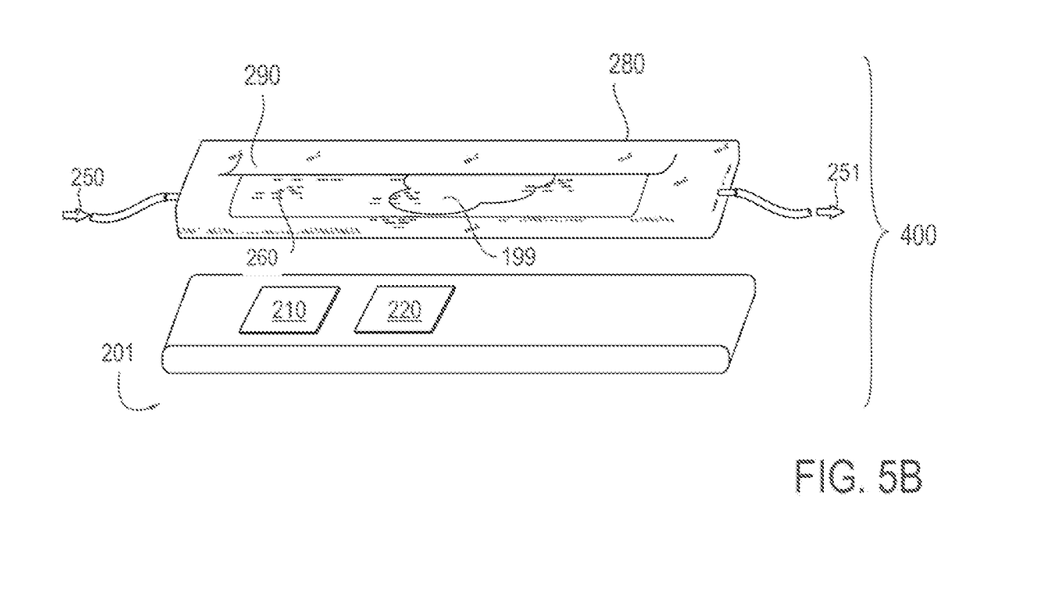
FIG. 5B is an assembled view of a flow cell adapted to use a fluid to sheath samples for MR Elastography in accordance with an embodiment of the present disclosure.

In another variation, as shown in FIGS. 4A-4B, a portion of a patient's body or a medical sample 199 may be partially ensheathed (i.e., covered or immersed) in a fluid 260. Alternatively, as shown in FIGS. 5A-5B, a portion of a patient's body or a medical sample 199 may be fully ensheathed or immersed in a fluid-filled vessel 280 to provide ample contact to transmit acoustic energy to the tissue sample during an MR scan. In such variations, the fluid 260 comprises one or more of: saline, ultrasound gel, mineral oil, or other ultrasound wave conductive substance or material.

In yet another variation, as shown in FIGS. 4A-5B, a patient 203 or sample 199 may interface with a fluid 260 on a gel pad 202 over the embedded sensor array 230 and provide an additional layer of conductance and comfort to a patient 203. The fluid 260 may comprise one or more of: saline, ultrasound gel, mineral oil, or other ultrasound conductive substance or material.

In one embodiment, in addition to the surface of the platform comprising a gel pad, a second RF transmitter or receiver coil, ultrasound transducer, or other sensor interface may be coated with gel or have a gel interface with the biological lifeform to enable the system to capture additional images of the biological lifeform. For example, in one embodiment, a clamshell may fold over a biological lifeform or a part of a patient's body. Alternatively, for example, a biological lifeform or a part of a patient's body may be inserted into a gel coated interface to provide better conductance for ultrasonic waves from multiple directions and an improved image or data capture quality.

As shown in an exploded view 300 in FIG. 4A and an assembled view 350 in FIG. 4B, a sample 199 may be positioned and translated through a fluid 260 on a gel pad 202, using positive or negative pressure in or on the gel pad 202 or fluid movement between a fluid source 250 and a fluid sink 251 to move or transport the biological lifeform, for example a sample 199, across the surface of the gel pad 202 with embedded sensor array 230. In some embodiments, the fluid 260 may flow from fluid source 250 to fluid sink 251 and function as a transport layer to move the sample across the sensor array 230, and the fluid 260 functions as a sheathing between the sample 199 and the sensor array 230. The fluid 260 may be at least partially contained in a tray, vessel, holder, encasement, or receptacle 270. The fluid 260 in the receptacle 270 may be open to the air or fully contained, so that the fluid 260 has an aseptic or sterile quality. The sample 199 may be disposed of along with the fluid 260, or the sample 199 may be cleaned and repackaged, vacuum-sealed, or otherwise processed (FFPE for example). Using the fluid 260 as a transport layer across the sensor array 230 allows an automation of measurements and a mechanical/physical queuing of sample measurements, which may dramatically increase throughput and productivity for a lab technician or the overall output of a lab facility (whether automated or not). Additionally, multiple samples may be transported in parallel or other packing arrangements to optimally utilize the sensor array 230 to take multiple measurements at once. Similarly, human or animal subjects may also be processed in rapid succession by floating across or through a sensor array 230, similar to how patrons of a water park float through a river ride or a waterslide.

As shown in an exploded view 400 in FIGS. 5A-5B, a biological lifeform, for example a sample 199, may be immersed or ensheathed in a fluid 260 and translated through a vessel 280 using a pump system, for example comprising a fluid source 250 and a fluid sink 251. The pump system may create a positive and/or negative pressure to propel the ensheathed sample 199 in a fluid 260, enabling a sample 199 to be transported (and also suspended in place) in a vessel 280. During transport through the vessel 280, ultrasound energy and/or RF energy may be applied to the sample 199 for performance of MR Elastography or other MR and non-MR measurements on a sample 199. Such a system 400 may enable many samples 199 to be processed in quick succession and either bottled directly in their fluid 260, cleaned of the fluid 260, disposed of (via incineration or hazardous waste collection), vacuum sealed for storage, or otherwise processed (FFPE for storage and analysis). In such embodiments, the fluid 260 may comprise water, saline, ultrasound fluid, mineral oil, other aqueous material, or other ultrasonic wave conductive material. In some embodiments, as shown in FIG. 5B, the vessel 280 may further include an access means 290, for example a door, portal, hatch, or sealable opening, so that the sample 199 may be deposited in the vessel 280 or retrieved from the vessel 280.

In some embodiments of one or more of the preceding methods, there may be additional or fewer operations. Furthermore, the order of the operations may be changed, and/or two or more operations may be combined into a single operation. In addition, in some of the preceding embodiments there are fewer components or more components, a position of a component is changed, and/or two or more components are combined.

In the preceding description, reference is made to "some embodiments." Note that "some embodiments" describes a subset of all the possible embodiments but does not always specify the same subset of embodiments.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. A method for capturing a magnetic-resonance (MR) Elastography measurement of a biological lifeform, the method comprising:

providing a platform, a gel pad on a surface of the platform, and a sensor array, wherein the sensor array comprises: at least one ultrasound transducer, and at least one radio-frequency (RF) transmitter and receiver coil, wherein the sensor array is embedded within the gel pad, and the gel pad comprises an aqueous material and is configured to provide mechanical impedance matching between the at least one ultrasound transducer and the biological lifeform, wherein the aqueous material transmits more ultrasound energy than glycerin, mineral oil or water, wherein at least the one ultrasound transducer and at least the one RF transmitter are embedded within the gel pad, and wherein embedded comprises surrounding and having contact with at least three sides of at least the one ultrasound transducer and at least the one RF transmitter;

generating one or more shear waves in the biological lifeform;

acquiring one or more images of a propagation of the one or more shear waves; and processing the one or more images to produce a quantitative map of a tissue stiffness of the biological lifeform.

2. The method of claim 1, further comprising identifying an anomaly in the biological lifeform based, at least in part, on the produced quantitative map.

3. The method of claim 1, further comprising altering a water content of the gel pad before or during capture of the MR Elastography measurement.

4. The method of claim 1, further comprising altering a composition of the gel pad with one or more of: a contrast agent, a substance with a known T1 and T2, and a known proton density.

5. The method of claim 1, further comprising altering one or more of: an elasticity and a viscosity of the gel pad to alter a surface area of the gel pad in contact with the biological lifeform.

6. The method of claim 1, wherein the sensor array further comprises one or more of: an optical sensor, an infrared sensor, a conductance sensor, a piezoelectric sensor, a movement sensor, a fiber optic sensor, a photoplethysmogram sensor, and an electrocardiogram sensor.

7. The method of claim 6, further comprising monitoring a pulse of the biological lifeform using the sensor array.

8. The method of claim 6, further comprising measuring one or more of: a weight, a volume, and a density of the biological lifeform using the sensor array.

9. The method of claim 6, wherein the gel pad comprises doping agent that conveys imaging phantom attributes to the gel pad.

10. The method of claim 6, wherein different regions of the gel pad comprise different concentrations of a doping agent.

11. The method of claim 6, wherein the gel pad comprises a doping agent to differentiate the gel pad from the biological lifeform.

* * * * *